(12) United States Patent
Morash

(10) Patent No.: US 9,545,288 B2
(45) Date of Patent: Jan. 17, 2017

(54) SYSTEMS AND DEVICES FOR A COUNTER BALANCED SURGICAL ROBOT

(71) Applicant: CUREXO TECHNOLOGY CORPORATION, Fremont, CA (US)

(72) Inventor: James P. Morash, Fremont, CA (US)

(73) Assignee: THINK SURGICAL, INC., Fremont, CA (US)

( * ) Notice: Subject to any disclaimer, the term of this patent is extended or adjusted under 35 U.S.C. 154(b) by 354 days.

(21) Appl. No.: 14/213,671

(22) Filed: Mar. 14, 2014

(65) Prior Publication Data

US 2014/0343567 A1 Nov. 20, 2014

Related U.S. Application Data

(60) Provisional application No. 61/786,180, filed on Mar. 14, 2013.

(51) Int. Cl.
*A61B 19/00* (2006.01)
*A61B 17/16* (2006.01)

(52) U.S. Cl.
CPC ........... *A61B 19/2203* (2013.01); *A61B 17/16* (2013.01); *A61B 34/30* (2016.02); *A61B 2034/2051* (2016.02); *A61B 2034/2055* (2016.02); *A61B 2090/504* (2016.02)

(58) Field of Classification Search
CPC ................. G05B 2219/45083; Y10S 901/08
USPC .......... 318/568.11, 568.1, 567, 560
See application file for complete search history.

(56) References Cited

U.S. PATENT DOCUMENTS

| 4,945,914 | A |   | 8/1990 | Allen |   |
|---|---|---|---|---|---|
| 4,991,579 | A |   | 2/1991 | Allen |   |
| 5,086,401 | A |   | 2/1992 | Glassman et al. |   |
| 5,094,241 | A |   | 3/1992 | Allen |   |
| 5,097,839 | A |   | 3/1992 | Allen |   |
| 5,113,424 | A | * | 5/1992 | Burdea | ..... A61B 6/08 378/168 |
| 5,119,817 | A |   | 6/1992 | Allen |   |

(Continued)

FOREIGN PATENT DOCUMENTS

WO 9107726 A1 5/1991

OTHER PUBLICATIONS

Thomas Ault, M. W. Siegel, "Frameless Patient Registration Using Ultrasonic Imaging", The Robotics Institute, School of Computer Science, Carnegie Mellon University, Pittsburgh, PA 15213; pp. 1-7, May 14, 1995.

(Continued)

*Primary Examiner* — David S Luo
(74) *Attorney, Agent, or Firm* — Avery N. Goldstein; Blue Filament Law PLLC

(57) ABSTRACT

Described herein are systems and devices for counterbalancing a surgical robotic system using a counterbalanced Z-axis drive. The counterbalanced Z-axis drive includes a self-centering ball screw assembly having a linear actuator and a counter weight. The counter weight is configured to substantially support a load associated with an arm of the robotic system when the driving portion is engaged or disengaged. In some embodiments, the counterbalanced Z-axis drive controls the arm and a movable effector mounted on the arm. Also disclosed herein are systems and devices for direct drive actuation of rotary axes of the arm which reduce the size and weight of the arm.

19 Claims, 11 Drawing Sheets

(56) References Cited

U.S. PATENT DOCUMENTS

| | | | |
|---|---|---|---|
| 5,142,930 | A | 9/1992 | Allen et al. |
| 5,198,877 | A | 3/1993 | Schulz |
| 5,211,164 | A | 5/1993 | Allen |
| 5,222,499 | A | 6/1993 | Allen et al. |
| 5,230,338 | A | 7/1993 | Allen et al. |
| 5,383,454 | A | 1/1995 | Bucholz |
| 5,397,323 | A | 3/1995 | Taylor et al. |
| 5,397,329 | A | 3/1995 | Allen |
| 5,769,092 | A | 6/1998 | Williamson, Jr. |
| 5,776,136 | A * | 7/1998 | Sahay .................... A61B 17/58 606/79 |
| 5,806,518 | A | 9/1998 | Mittelstadt |
| 5,824,085 | A | 10/1998 | Sahay et al. |
| 6,033,415 | A | 3/2000 | Mittelstadt et al. |
| 6,242,879 | B1 * | 6/2001 | Sagues .................. G03F 7/7075 318/567 |
| 6,436,107 | B1 | 8/2002 | Wang et al. |
| 6,539,333 | B1 | 3/2003 | Metelski |
| 6,831,436 | B2 * | 12/2004 | Gonzalez ................ B25J 9/041 318/567 |
| 9,125,679 | B2 * | 9/2015 | Larkin ................ A61B 19/2203 |
| 2011/0152871 | A1 | 6/2011 | Park et al. |

OTHER PUBLICATIONS

P. Cain, P. Kazanzides, J. Zuhars, B. Mittelstadt, and H. Paul, "Safety Considerations in a Surgical Robot", Integrated Surgical Systems, Inc., Sacramento, CA; © ISA, 1993—Paper #93-035, 0067-8856/93/291-294/$0 + .50pp.

E. Grimson, T. Lozano-Pèrez, W. Wells, G. Ettinger, S. White, R. Kikinis "Automated Registration for Enhanced Reality Visualization in Surgery"; from AAAI Technical Report SS-94-05. Compilation copyright © 1994, AAAI (www.aaai.org), pp. 26-29.

P. Kazanzides, J. Zuhars, B. Mittelstadt, S. Williamson, P. Cain, F. Smith, L. Rose, B. Musits "Architecture of a Surgical Robot", Integrated Surgical Systems, Inc., 829 W. Stadium Lane, Sacramento, CA 95834; 0-7803-0720-8/92 $3.00 @1992 IEEE, pp. 1624-1629.

Peter Kazanzides, Joel Zuhars, Brent Mittelstadt, and Russell H. Taylor "Force Sensing and Control for a Surgical Robot", Integrated Surgical Systems, 829 West Stadium Lane, Sacramento, CA 95834, USA, IBM T.J. Watson Research Center, P.O. Box 702, Yorktown Heights, NY 10598; proceedings of the 1992 IEEE international Conference on Robotics and Automation, Nice, France, May 1992, pp. 612-617.

Peter Kazanzides, Brent D. Mittelstadt, Joel F. Zuhars, Phillip W. Cain, Howard A. Paul "Surgical and Industrial Robots: A Comparison and Case Study", Integrated Surgical Systems, Inc., 829 W. Stadium Lane, Sacramento, CA 95834; 1993 International Robots and Vision Automation Conference, Detroit, Michigan, 9 pages.

S. Lavallée, Ph.D., P. Sautot, Ph.D., J. Troccaz, Ph. D., P. Cinquin, Ph.D., M.D., and P. Merloz. M.D., "Computer-Assisted Spine Surgery: A Technique for Accurate Transpedicular Screw Fixation Using CT Data and a 3-D Optical Localizer", Faculte de Medécine de Grenoble, TIMC-IMAG (S.L., P.S., J.T., P.C.), La Tronche, France: Service de Chirurgie Orthopedique, Chu (P.M.), Grenoble, La Tronche, France, Journal of Image Guided Surgery, 1:65-73 (1995), downloaded from informahealthcare.com by Standford University on Mar. 3, 2015.

Jon T. Lea, Dane Watkins, Aaron Mills, Michael A. Peshkin, Thomas C. Kienzle III, S. David Stulberg "Registration and Immobilization in Robot-Assisted Surgery", Department of Mechanical Engineering, Northwestern University, Evanston; IL 60208; Department of Orthopedic Surgery, Northwestern University Medical School, Chicago, IL 60611, Journal of Image Guided Surgery 1 (2), pp. 80-87, 1995.

Brent Mittelstadt, Howard Paul, Peter Kazanzides, Joel Zuhars, Bill Willamson, Robert Pettitt, Phillip Cain, David Kloth, Luke Rose and Bela Musits (1993), "Development of a Surgical Robot for Cementless Total Hip Replacement", Robotica / vol. 11/ Issue 06/ Nov. 1993, pp. 553-560; http://journals.cambridge/org/abstract_S02635744700019408; published on-line: Mar. 9, 2009.

Brent Mittelstadt, Peter Kazanzides, Joel Zuhars, Phillip Cain, Bill Williamson "Robotic Surgery: Achieving Predictable Results in an Unpredictable Environment", Integrated Surgical Systems, Inc., 829 W. Stadium Lane, Sacramento, CA 95834, USA; '93 ICAR, pp. 367-372.

Howard A. Paul, D.V.M,, William L. Bargar, M.D., Brent Mittlestadt, Bela Musits, Russell Taylor, Ph.D., Peter Kazanzides, Ph.D., Joel Zuhars, Bill Williamson, William Hanson, M.S. "Development of a Surgical Robot for Cementless Total Hip Arthroplasty", Clinical Orthopaedics and Related Research, No. 285, pp. 57-66, Dec. 1992.; Integrated Surgical Systems, Sacramento, CA; IBM T.J. Watson Research Center, Yorktown Heights, New York; IBM Palo Alto Science Center, Palo Alto, California.

David A. Simon, Martial Hebert; Takeo Kanade "Techniques for Fast and Accurate Intra-Surgical Registration, Robotics Institute", Carnegie Mellon University, Pittsburgh, PA 15213; The Journal of Image Guided Surgery, vol. 1, No. 1,—Apr. 1995, 19 pages.

* cited by examiner

SYSTEMS AND DEVICES FOR A COUNTER BALANCED SURGICAL ROBOT

RELATED APPLICATIONS

This application is a non-provisional application that claims priority benefit of U.S. Provisional application Ser. No. 61/786,180 filed 14 Mar. 2013; the contents of which are hereby incorporated by reference.

INCORPORATION BY REFERENCE

All publications and patent applications mentioned in this specification are herein incorporated by reference in their entirety, as if each individual publication or patent application was specifically and individually indicated to be incorporated by reference in its entirety.

TECHNICAL FIELD

This invention relates generally to surgical bone cutting systems, and more particularly to systems for counterbalancing a vertical axis of motion of the system.

BACKGROUND

Robotic systems for assisting in a number of medical procedures have been proposed, including neurosurgical, laparoscopic, and orthopedic procedures. When performing robotically assisted surgery, (for example, total hip replacement when cutting a cavity into a patient's femur bone for the insertion of an artificial hip joint therein), it is very important to balance the weight of a moving extended arm so the system does not tip. Various types of robots use counterbalance weights, gas springs and mechanical springs to help achieve this balance.

It is also important to consider the robot's vertical axis of motion, for example a robot having a vertical axis of motion that does not need a separate high precision Z axis at the robot wrist and makes the robot arm easier to reposition manually when necessary. For example, some existing arm designs have two separate vertical (Z-axis) actuators: a high precision drive at the wrist, and a lower precision lifting column actuator (with high moment load rating) at the base of the robot arm's vertical pedestal. The base column is used for gross positioning, and the wrist Z is used for fine positioning. In the event that the vertical position of the robotic arm must be manually adjusted, the user must reach up and release a brake lever, causing the wrist Z to drop freely under its own weight (unless hand-held in place).

Accordingly, it has been desirable to attempt to counter balance the robot's vertical axis of motion while making the robot arm easier to reposition manually when necessary.

The ORTHODOC presurgical planning workstation and the ROBODOC robotic surgical system are described in a number of references, including the following: (1) Kazanzides, P., Zuhars, J., Mittelstadt, B. D., Taylor, R. H.: "Force Sensing and Control for a Surgical Robot," Proc. IEEE Conference. on Robotics & Automation, Pages 612-616, Nice, France, May 1992. (2) Kazanzides, P., Zuhars, J., Mittelstadt, B. D., Williamson, B., Cain, P., Smith, F., Rose, L., Mustis, B.: "Architecture of a Surgical Robot," Proc. IEEE Conference. on Systems, Man, and Cybernetics, Chicago, Ill., Pages 1624-1629, October, 1992. (3) Paul, H. A., Bargar, W. L., Mittelstadt, B., Musits, B., Taylor, R. H., Kazanzides, P., Zuhars, J., Williamson, B., Hanson, W.: "Development of a Surgical Robot For Cementless Total Hip Arthroplasty," Clinical Orthopaedics, Volume 285, Pages 57-66, December 1992. (4) Kazanzides, P., Mittelstadt, B. D., Zuhars, J., Cain, P., Paul, H. A., "Surgical and Industrial Robots: Comparison and Case Study," Proc. International Robots and Vision Automation Conference, Pages 1019-1026, Detroit, Mich., April 1993. (5) Mittelstadt, B., Kazanzides, P., Zuhars, J., Williamson, B., Pettit, R., Cain, P., Kloth, D., Rose, L., Musits, B.: "Development of a surgical robot for cementless total hip replacement," Robotica, Volume 11, Pages 553-560, 1993. (6) Mittelstadt B., Kazanzides, P., Zuhars, J., Cain, P., Williamson, B.: "Robotic surgery: Achieving predictable results in an unpredictable environment," Proc. Sixth International Conference on Advanced Robotics, Pages 367-372, Tokyo, November, 1993. (7) Cain, P., Kazanzides, P., Zuhars, J., Mittelstadt, B., Paul, H.: "Safety Considerations in a Surgical Robot," Biomedical Sciences Instrumentation, Volume 29, Pages 291-294, San Antonio, Tex., April 1993. (8) Mittelstadt, B. D., Kazanzides, P., Zuhars, J., Williamson, B., Cain, P., Smith, F. Bargar, W.: "The Evolution of A Surgical Robot From Prototype to Human Clinical Use," in Proc. First International Symposium on Medical Robotics and Computer Assisted Surgery, Volume I, Pages 36-41, Pittsburgh, Pa., September 1994.

Other publications which describe image registration in robotic surgical and other procedures include the following: (9) Grimson, W. E. L., Lozano-Perez, T., Wells III, W. M., Ettinger, G. J., White, S. J., Kikinis, R.: "Automated Registration for Enhanced Reality Visualization in Surgery," Proceedings of the First International Symposium on Medical Robotics and Computer Assisted Surgery, Volume I, Sessions I-III, Pages 82-89, Pittsburgh, Pa., Sep. 22-24, 1995. (10) Nolte, L. P., Zamorano, L. J., Jiang, Z., Wang, Q., Langlotz, F., Arm, E., Visarius, H.: "A Novel Approach to Computer Assisted Spine Surgery," Proceedings of the First International Symposium on Medical Robotics and Computer Assisted Surgery, Volume II, Session IV, Pages 323-328, Pittsburgh, Pa., Sep. 22-24, 1994. (11) Lavallee, S., Sautot, P., Troccaz, J., Cinquin, P., Merloz, P.: "Computer Assisted Spine Surgery: a technique for accurate transpedicular screw fixation using CT data and a 3-D optical localizer," Proceedings of the First International Symposium on Medical Robotics and Computer Assisted Surgery, Volume II, Session IV, Pages 315-321, Pittsburgh, Pa., Sep. 22-24, 1994. (12) Potamianos, P., Davies, B. L., Hibberd, R. D.: "Intra-Operative Imaging Guidance For Keyhole Surgery Methodology and Calibration," Proceedings of the First International Symposium on Medical Robotics and Computer Assisted Surgery, Volume I, Sessions I-III, Pages 98-104, Pittsburgh, Pa., Sep. 22-24, 1994. (13) Simon, D. A., Hebert, M., Kanade, T.: "Techniques for Fast and Accurate Intra-Surgical Registration," Proceedings of the First International Symposium on Medical Robotics and Computer Assisted Surgery, Volume I, Sessions I-III, Pages 90-97, Pittsburgh, Pa., Sep. 22-24, 1995. (14) Peria, O., Francois-Joubert, A., Lavallee, S., Champleboux, G., Cinquin, P., Grand, S.: "Accurate Registration of SPECT and MR brain images of patients suffering from epilepsy or tumor," Proceedings of the First International Symposium on Medical Robotics and Computer Assisted Surgery, Volume II, Session IV, Pages 58-62, Pittsburgh, Pa., Sep. 22-24, 1995. (15) Lea, J. T., Watkins, D., Mills, A., Peshkin, M. A., Kienzle III, T. C., Stulberg, D. S.: "Registration and Immobilization for Robot-Assisted Orthopaedic Surgery," Proceedings of the First International Symposium on Medical Robotics and Computer Assisted Surgery, Volume I, Sessions I-III, Pages 63-68, Pittsburgh, Pa., Sep. 22-24, 1995. (16) Ault, T., Siegel, M. W.: "Frameless Patient Registration Using Ultrasonic Imaging," Proceedings of the First International Symposium on Medical Robotics and Computer Assisted Surgery, Volume I, Sessions I-III, Pages 74-81, Pittsburgh, Pa., Sep. 22-24, 1995. (17) Champleboux, G., Lavallee, S., Cinquin, P.: "An Optical Conformer for Radiotherapy Treatment Planning," Proceedings of the First International Symposium on Medical Robotics and Computer Assisted Surgery, Volume I, Sessions I-III, Pages 69-73, Pittsburgh, Pa., Sep. 22-24, 1995.

Various systems for image registration using fiducial implants are also described in U.S. Pat. Nos. 4,991,579; 4,945,914; 5,094,241; 5,119,817; 5,097,839; 5,142,930; 5,211,164; 5,230,338; 5,222,499; and 5,397,329 to Allen.

A system and method for performing robotically assisted surgery is described in U.S. Pat. No. 5,086,401. Computer-assisted imaging and probe tracking systems are described in U.S. Pat. Nos. 5,383,454; 5,198,877; and WO 91/07726. Copending and recently allowed application Ser. No. 08/526,826, assigned to the assignee of the present application, describes a method and system for transforming a bone image into a robotic coordinate system by aligning a robotic probe within the medullary canal of the femur. Patent application Ser. No. 09/022,643, also assigned to the assignee of the present application, describes a method and system for transforming a bone image into a robotic coordinate system based upon registering between the robotic coordinate system and the image data set 1) two positional coordinates axially spaced apart along the bone and 2) a directional vector passing through at least one of the positional coordinates.

Thus, there is a need for an improved system and method for a counterbalanced surgical robotic system using an actuator that is both precise enough for accurate cutting, and strong enough to handle the moment load of the cantilevered robot arm, with a range of motion sufficient to increase overall workspace compared to existing robotic arms. In addition, in some instances it is important to minimize the size and weight of the robot base, as well as reducing the overall weight of the arm. This invention provides such a new and useful system and method.

DETAILED DESCRIPTION

Figure 1:
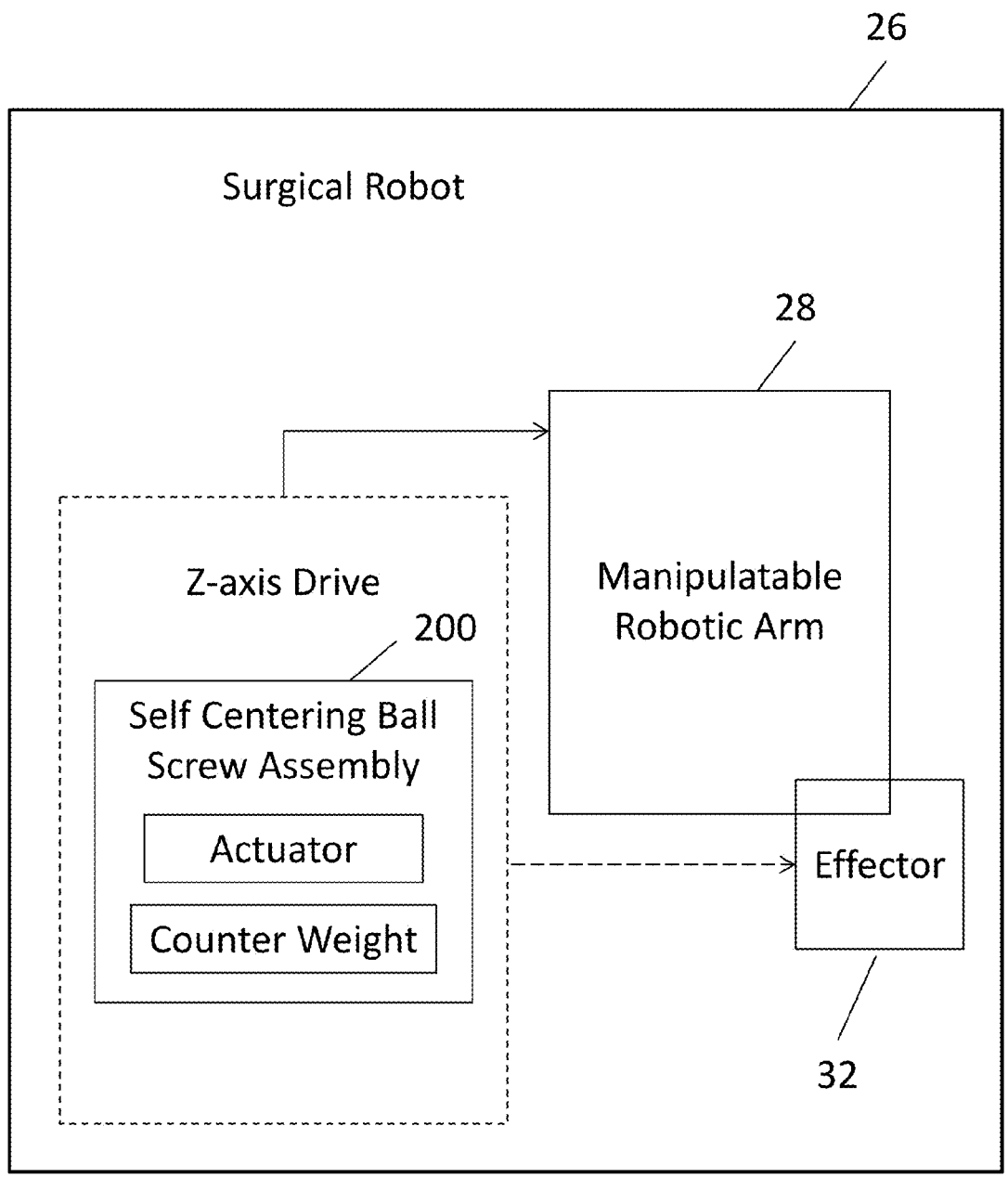
FIG. 1 illustrates a surgical robotic system in accordance with a preferred embodiment.

The following description of the preferred embodiments of the invention is not intended to limit the invention to these preferred embodiments, but rather to enable any person skilled in the art to make and use this invention. The present invention has utility as counter balanced surgical robotic systems and devices. Also described herein are systems and devices for counterbalancing a surgical robotic system using counter-weighted precision Z-axis drive design and a self-centering ball screw assembly.

In general, the devices may include a manipulatable arm and a rail assembly having a shaft that engages a first carriage and a second carriage via threaded mechanism. The first carriage supports the manipulatable arm and has a Z-axis drive actuator that controls a vertical axis of motion (or vertical position) of at least one of the manipulatable arm and an effector mounted to the manipulatable arm. The second carriage supports a counter weight and moves in a direction opposite that first carriage when the Z-axis drive actuator is engaged. The counter weight is selected to balance a weight and/or load of the manipulatable arm.

One inventive concept described herein is to counter-weight the robot's vertical axis of motion, in order to make it easier for a user to move the arm against gravity. This approach is particularly applicable to SCARA designs (such as the ROBODOC robotic arm).

The existing ROBODOC robotic arm design has two separate vertical (Z-axis) actuators: a high precision ballscrew drive at the wrist, and a lower precision lifting column actuator (with high moment load rating) at the base of the robot arm's vertical pedestal. The base column is used for gross positioning, and the wrist Z is used for fine positioning. In the event that the vertical position of the robotic arm must be manually adjusted, the user must reach up and release a brake lever, causing the wrist Z to drop freely under its own weight (unless hand-held in place).

The devices and systems described herein eliminate the redundancy of the two separate vertical actuators, using a single actuator that is both precise enough for accurate cutting, and strong enough to handle the moment load of the cantilevered robot arm, with a range of motion sufficient to increase overall workspace compared to existing robotic arms.

Thus, the devices and systems described herein may be advantageous as they remove the need for a separate high precision Z axis at the robot wrist and make the robot arm easier to reposition manually when necessary.

In addition, the design provides for significant load inertia but the substantially weightless design provides a smoother motion (e.g., reduced shaking)

Further, the high precision linear profile rails (or shafts) with ball guides provide for extremely accurate motion and high moment load capacity.

In addition, the overall height of the arm can be significantly reduced, by eliminating the Z axis from the robot wrist compared to the existing ROBODOC robotic arm. For example, to accommodate the 250 mm range of motion of the wrist Z, there has to be a greater-than-250 mm-high protrusion at the end of the arm. This may help to improve workspace for TKA and for future indications. The overall weight of the arm is also significantly reduced, which may enable reduction of the size and weight of the robot base.

As shown in FIG. 1, a surgical robotic system of a preferred embodiment may include a manipulatable arm 28 that carries a movable effector 32, and a counterbalanced Z-axis drive including a self-centering ball screw assembly 200. The counterbalanced Z-axis drive controls at least one of the manipulatable arm 28 or the movable effector 32. The system/device preferably functions to provide accurate vertical position control of a robot arm. In some embodiments, the system/device preferably functions to allow the arm to feel substantially weightless when manually repositioned. The preferred system/device is preferably used for surgical robotic system, but may alternatively be used for any suitable applications, clinical or otherwise. The system/device can be configured and/or adapted to function for any suitable robotic system.

Surgical Robot

Figure 2:
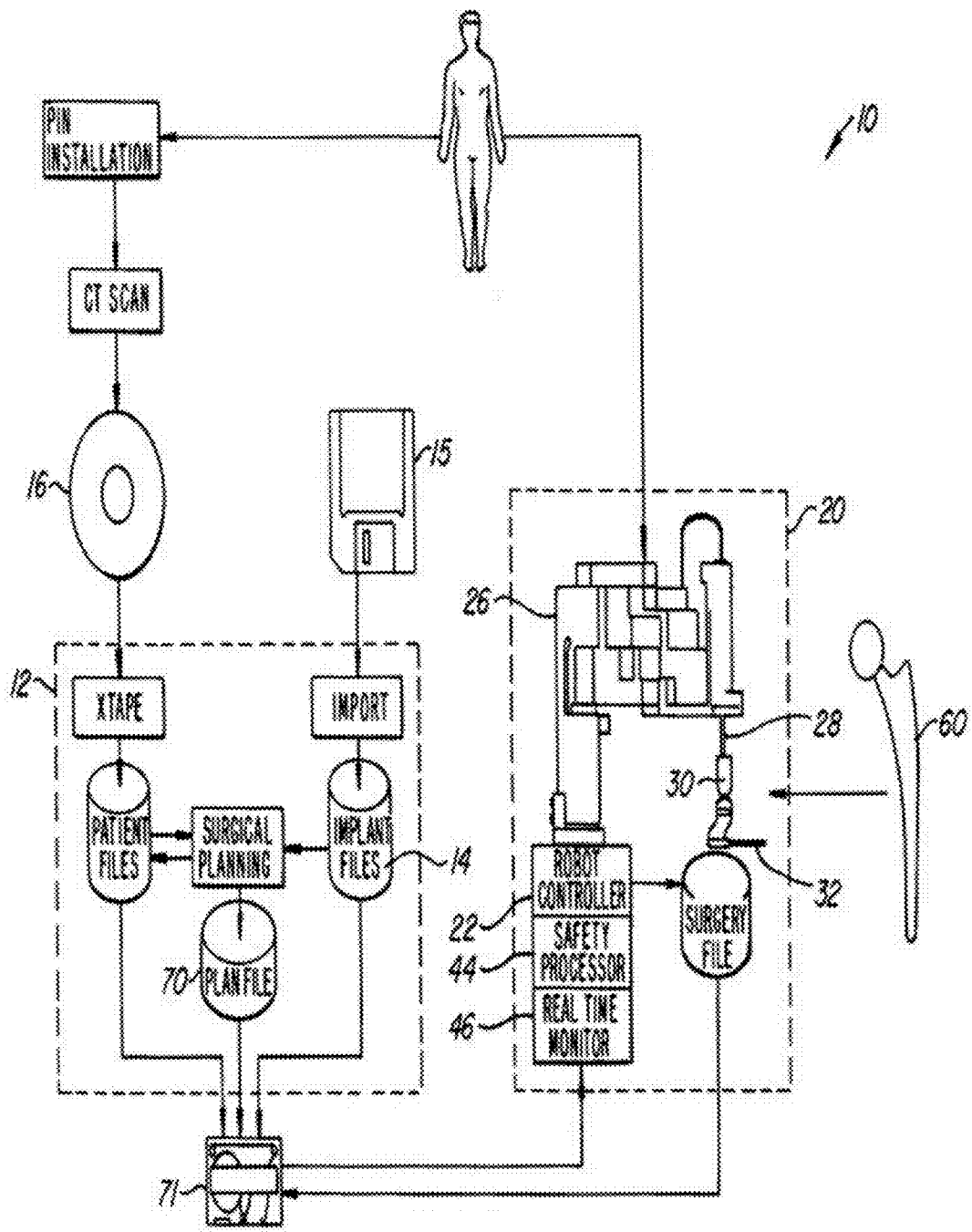
FIG. 2 illustrates the architecture of the surgical robotic system in accordance with a preferred embodiment.

As described, for example, in commonly owned U.S. Pat. Nos. 6,033,415; 5,824,085; 5,806,518; 5,776,136; and 5,769,092, an exemplary system 10 capable of implementing the methods of the present invention for robotic assisted surgery is illustrated in FIG. 2. The system 10 includes both a presurgical planning workstation 12 and a library of implant designs 14, for example, in the form of CAD model data sets 15. A bone image data set 16, for example representative of a CT bone image, is obtained and transferred into the presurgical planning workstation 12. The user, such as a treating physician or an assistant working with the treating physician, is able to work at the presurgical planning workstation to select and position a suitable implant design within the patient femur. Details of such presurgical planning are well described in the literature relating to the ORTHODOC presurgical planning system cited above.

The system 10 of the present invention further comprises a robotic operative system 20 which includes a robotic controller 22 (for example, a digital processor in the form of a programmable computer), an online display screen 24, and a robot 26. The robot can be any conventional industrial robot having a manipulatable surgical robotic arm 28 preferably having at least 5 axes and capable of high precision placement. A suitable surgical robotic is available from Sankyo Robotics with the model designation SR-5427-ISS. In some embodiments, a force sensor 30 is mounted at the distal end of arm 28, and an effector in the form of a probe 32 or a surgical cutting tool (not illustrated) may be attached to the force sensor.

The robotic system 20 further includes a safety processor 44, and a real time monitoring computer 46, as illustrated in FIG. 2. The force sensor 30, the safety processor 44, the real time monitor 46, and a bone motion monitor 50, each help monitor the position, slippage, and blockage of the effector end of the manipulatable arm 28. In some embodiments, the bone 60 (e.g. a femur) is held in place in a fixator assembly 52. Real time monitoring of these parameters can help assure that the robotic system is operating as planned. Details of these monitoring systems are described in the literature cited above which describes the ROBODOC robotic surgical system.

In some embodiments, a digitized bone data set which comprises the coordinate positions of a number of surface locations on the bone as measured by a bone digitizer arm registered to the robotic coordinate system. Accordingly, system 10 further includes bone digitizer arm 100, for example, as described in commonly owned U.S. Pat. No. 6,033,415. An acquired digitized bone data set 17, (shown in FIG. 2 as an input to robotic controller 22), is obtained by bone digitizer arm 100 and is used to transform bone image data set 16 into the robotic coordinate system.

Figure 3:
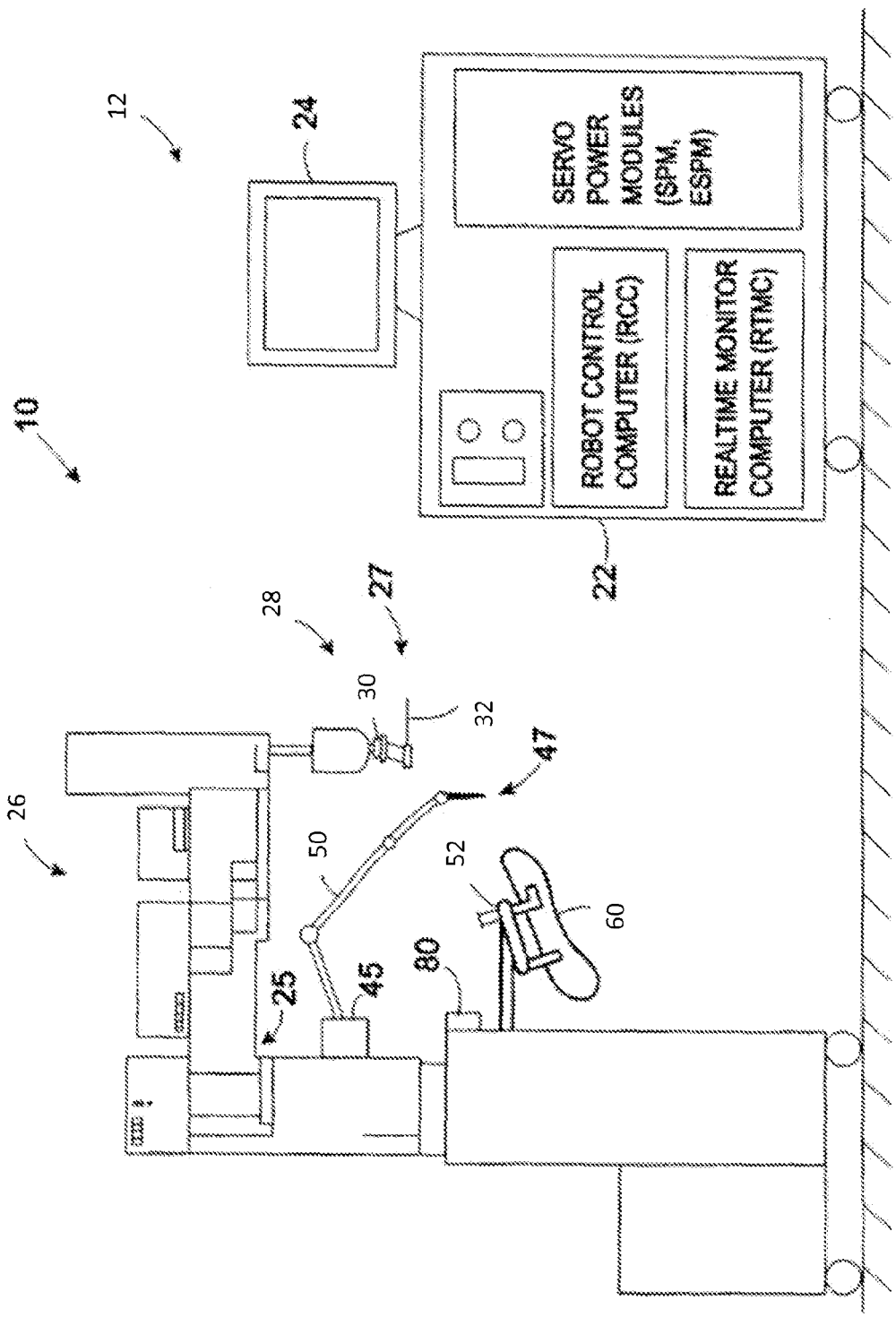
FIG. 3 illustrates the surgical components of the surgical system of FIG. 2 in accordance with a preferred embodiment.

As seen in FIG. 3 the system 10 comprises a passive mechanical arm bone motion detector 50 and a bone fixator 52. The preplanning workstation (user interface) 12 comprises a computer 17 and a terminal display 24.

Cutting tool 32 on surgical robotic arm 28 is adapted to cut an implant cavity into the end of bone 60. Fixator 52 is adapted to hold bone 60 in a substantially fixed position during surgery. Each of surgical robotic arm 28, passive mechanical arm 50 and fixator 52 are attached at their proximal ends to robot 26 which acts as a fixed base, preventing any relative motion between proximal ends 25 and 45 of surgical robotic arm 28 and passive mechanical arm 50, respectively.

Connection of both proximal end 45 of passive mechanical arm 50 and proximal end 25 of surgical robotic arm 28 to robot 26 avoids relative motion between ends 25 and 45, such that surgical robotic arm 28 and passive mechanical arm 50 move in the same relative coordinate system.

Figure 4A:
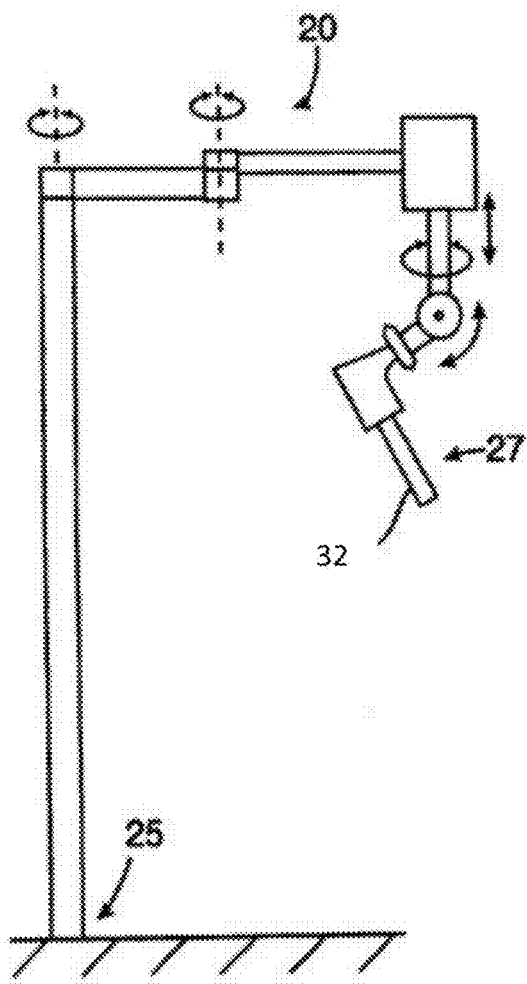
FIGS. 4A-4B illustrate a manipulatable arm and the axes of rotation in accordance with a preferred embodiment.
Figure 4B:
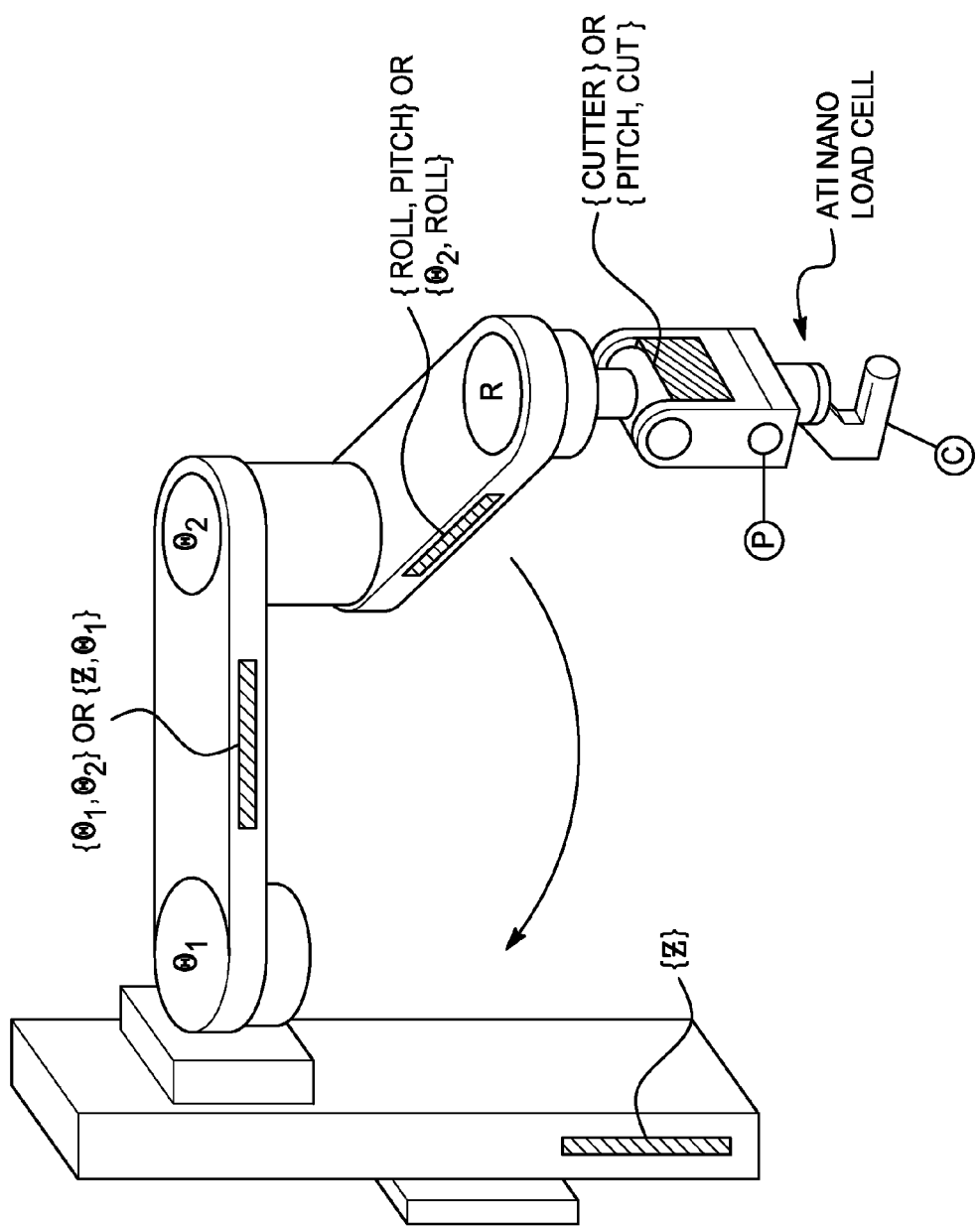

Referring to FIGS. 4A and 4B, surgical robotic arm 28 is also adapted for movement in five or six degrees of freedom. Surgical robotic arm 28 has a proximal end 25 which is fixed to robot 26 and a distal end 27 which can be controllably moved to desired locations such that the position of movable distal end 27 relative to fixed proximal end 25 will be constantly known. The manipulatable arm 28 is discussed in more detail below.

Counter Balanced Z-Axis Drive and Self-Centering Ball Screw Assembly

Figure 5A:
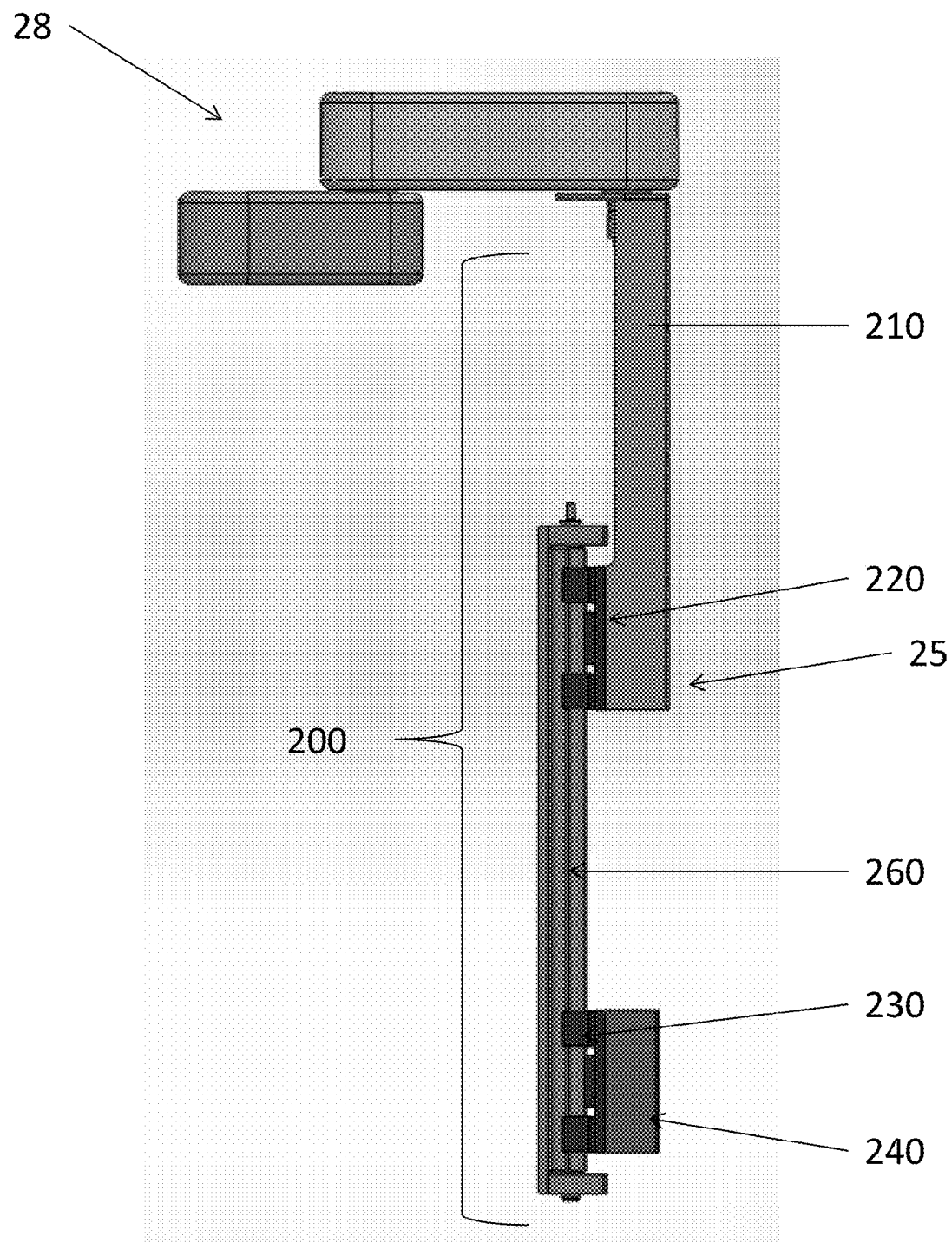
FIG. 5A-5B illustrate a counterweighted precision Z axis drive and a self-centering ball screw assembly in accordance with a preferred embodiment.
Figure 5B:
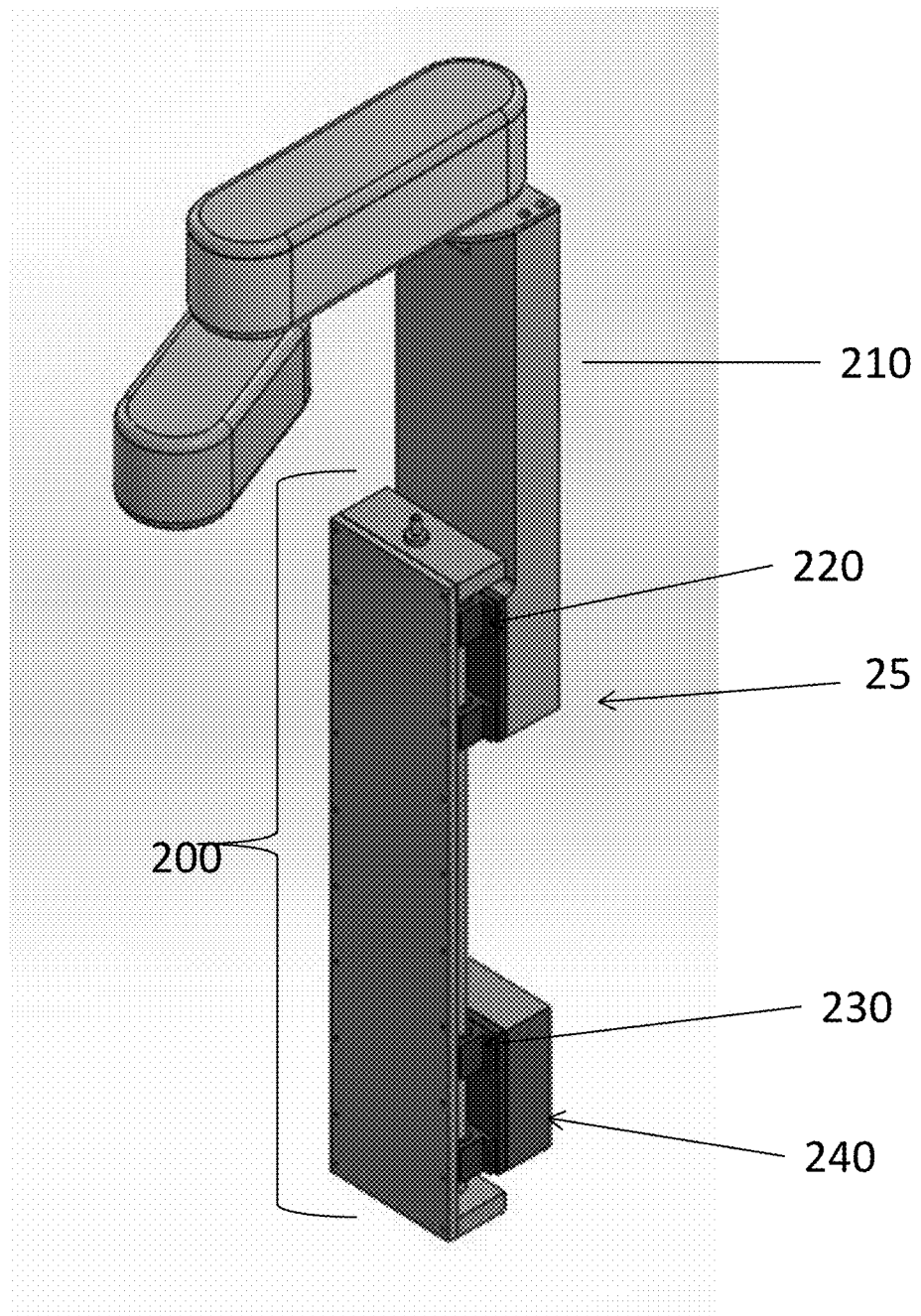

FIGS. 5A and 5B illustrate a preferred embodiment of a counter balanced Z-drive actuator including a self-centering ball screw assembly 200 for a surgical robotic system. The self-centering ball screw assembly includes a first carriage 220 configured to carry and support the manipulatable arm 28 and a Z-axis actuator (not shown) to drive the linear position of the manipulatable arm 28 along a Z-axis. The weight of the first carriage 220 and the objects carried by it are counterbalanced by a second carriage 230 configured to carry a counter weight 240. The first carriage 220 and second carriage 230 engage a shaft 260 (e.g., a shaft of a rail assembly) through a threaded mechanism. In some embodiments, as the first carriage 220 engages and moves in a linear direction along the shaft, the second carriage 230 moves in an opposite linear direction along the shaft. In some embodiments, the self-centering ball screw assembly 200 includes a first carriage 220 configured to carry the manipulatable arm 28 and a second carriage 230 configured to carry the counter weight 240.

As shown in FIG. 5B, the first carriage 220 supports and carries the manipulatable arm via backbone 210. For example, the manipulatable arm 28 can be mounted to the first carriage 220 using the backbone structure. In the illustrated example, a bottom end of the backbone 210 is attached to the first carriage 220. For example, the bottom end of the backbone 210 can be bolted to the first carriage 220 with a sufficient quantity of fasteners to be rigid. A top end of the backbone 210 is attached to a first motor shaft, such as the theta 1 motor shaft. For example, the top end of the backbone 210 can be attached to the Theta1 motor shaft using a large-bore clamp with an alignment pin. In some embodiments, the backbone 210 is attached to the proximal end of the manipulatable arm 25. In some embodiments, backbone 210 is the proximal end of the manipulatable arm 25.

The backbone 210 can be configured to achieve a desired stiffness and to control vibration characteristics of the backbone 210 and manipulatable arm 28. In some embodiments, the backbone is hollow allowing cables to be passed through a cable path in the backbone.

Actuator

The Z-axis actuator of the first carriage 220 can be a linear direct drive actuator. The linear actuator (or drive motor) is configured to create a motion along a Z-axis. For example, the linear actuator can be configured to control a linear position of the manipulatable arm 28.

In some embodiments, the linear actuator is configured to control the linear position of the manipulatable arm 28 and a linear position of the effector 32. In such embodiments, a classic SCARA wrist Z axis actuator can be eliminated in favor of a single high precision "base lift". Removing the Z axis actuator from the robot wrist will significantly reduce the overall size and weight of the robot arm 28.

The size of the linear drive motor can be selected to provide desired characteristics. For example, the size may be selected to provide a torque high enough to provide sufficient control authority, since a load can exceed two times a mass of the robot arm 28.

Counter Weight

The counter weight 240 is configured to support a load associated the system. In some embodiments, the counter weight 240 is configured to substantially support a load associated with the manipulatable arm 28 when the driving portion is engaged or disengaged.

The counter weight 240 can be made from any suitable material that achieves desired characteristics. In some embodiments, the counterweight is a solid block of lead. In some embodiments, the counterweight has a size configured to balance the weight of the manipulatable arm.

The weight reduction from removing the wrist Z-axis actuator, combined with the placement of the counterweight of equal or greater mass on the lower carriage, allows for the overall size of the robot base to be reduced, while still preventing the robot from tipping over, for example, when the manipulatable arm is fully extended. Thus, in some embodiments, the footprint of the device and system will be reduced. It will be appreciated that a reduced footprint can be advantageous, for example, in operating rooms.

Counter-Balancing Mechanism

A threaded mechanism can be used to engage the carriages 220, 230 with the shaft 260. A ball screw is one acceptable threaded mechanism.

Figure 6A:
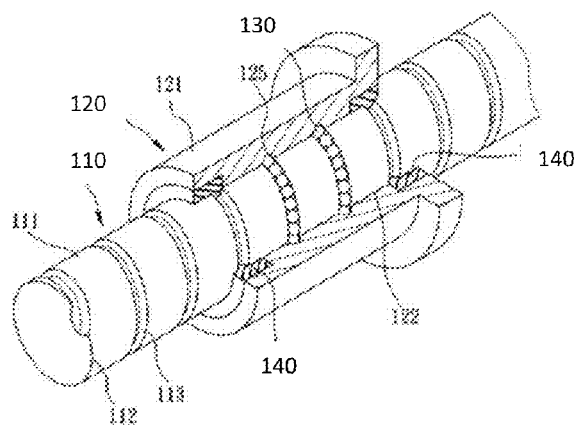
FIG. 6A-6C illustrate ball screws including a single lead, twin lead, and triple lead ball screw in accordance with a preferred embodiments.

Referring to FIG. 6A, a first conventional ball screw includes a screw shaft 110, a ball nut 120 rotatably sleeved on the screw shaft 110, a plurality of bearing balls 130 disposed between the screw shaft 110 and the ball nut 120, and scrapers 140. The screw shaft 110 includes a shaft body 111 with an outer shaft surface 112 formed with a helical raceway 113. The screw nut 120 includes a nut body 121 with an inner nut surface 122 formed with a ball groove 125 that corresponds to and complements with the helical raceway 113. The bearing balls 130 are rollably disposed between the ball groove 125 and the helical raceway 113. The scrapers 140 are disposed at the inner nut surface 122.

Figure 6B:
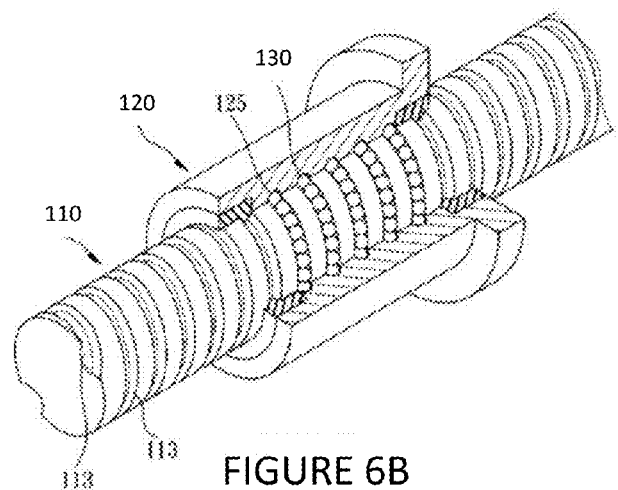

Referring to FIG. 6B, a second conventional ball screw is shown to be similar to the first conventional ball screw. The second conventional ball screw is a twin-lead ball screw, whose screw shaft 110 includes two helical raceways 113, whose screw nut 120 includes two ball grooves 125 that respectively correspond to and complement with the helical raceways 113, and whose bearing balls 130 are respectively disposed between the helical raceways 113 and the ball grooves 125 corresponding thereto. The ball screw is suited for high-load applications due to simultaneous use of the two helical raceways 113.

Figure 6C:
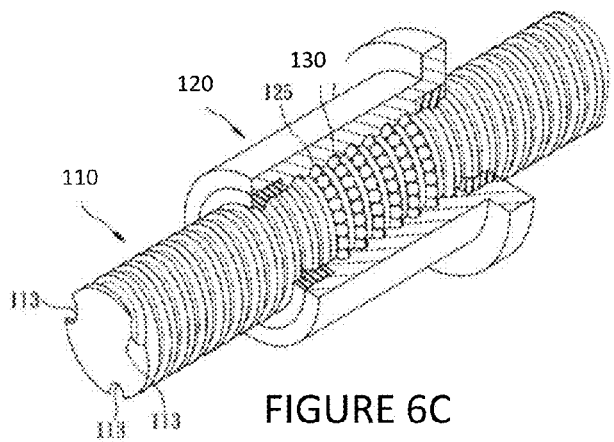

Referring to FIG. 6C, a third conventional ball screw is shown to be similar to the first conventional ball screw. The third conventional ball screw is a high-lead ball screw, whose screw shaft 110 includes three helical raceways 113, whose screw nut 120 includes three ball grooves 125 that respectively correspond to and complement with the helical raceways 113, and whose bearing balls 130 are respectively disposed between the helical raceways 113 and the ball grooves 125 corresponding thereto. The ball screw is suited for high lead applications due to simultaneous use of the three helical raceways 113.

Figure 7:
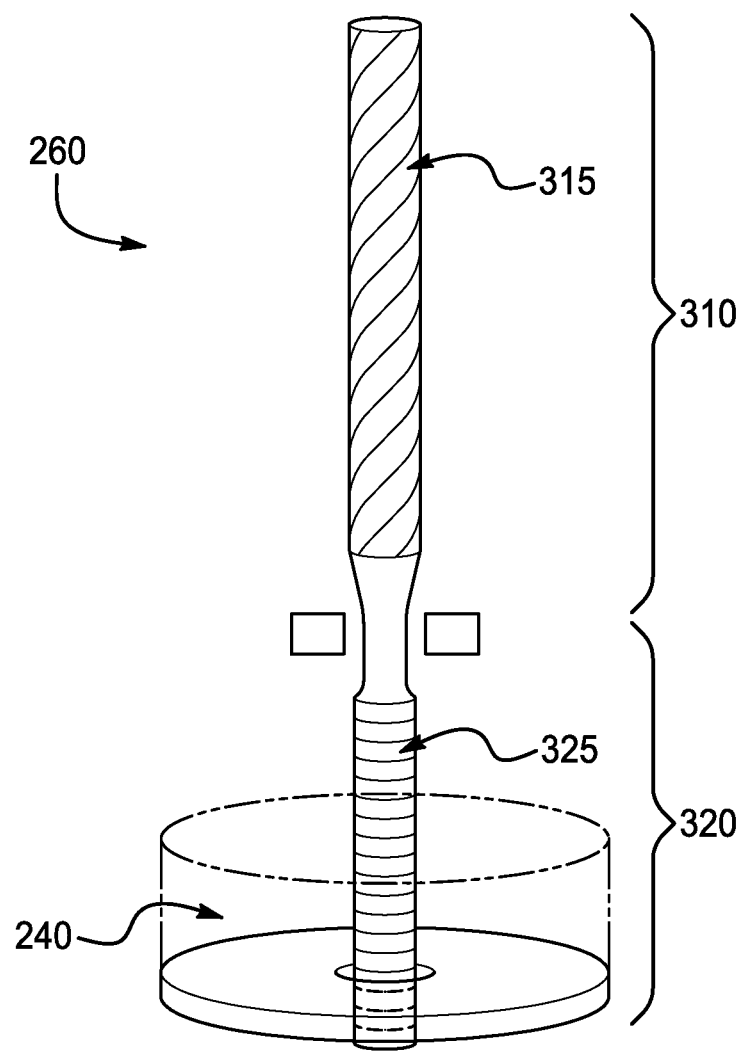
FIG. 7 illustrates a ball screw assembly having two different lead pitches in accordance with a preferred embodiment.

As shown in FIG. 7, in some embodiments, the shaft 260 has a first portion 310 with a first thread 315 and a second portion 320 with a second thread 325 in a direction opposite the first thread. For example, the first thread may be a standard or right handed thread, while the second thread may be a left handed thread. In some embodiments, the first carriage engages the first portion of the shaft and the second carriage engages the second portion of the shaft. As a result, when the shaft is turned the first carriage 220 engaging the first portion 315 of the shaft moves in a direction opposite the second carriage 230 engaging the second portion 325 of the shaft. In some embodiments, the first portion 310 includes a first screw and the second portion 320 includes a second screw. In such embodiments, the first portion 310 and the second portion 320 can be joined end to end, for example, with rigid couplings to form a single shaft 260.

Use of Different Thread Pitches

In some embodiments, a lead pitch of the first thread is different than a lead pitch of the second thread. For example, as shown in FIG. 7, the lead pitch of the first thread is larger than the lead pitch of the second thread. In such embodiments, the second carriage (and the counter-weight) need only travel one-half or one-third the vertical distance traveled by the first carriage (and manipulatable arm).

In other embodiments, the lead pitch of the first thread is substantially the same as the lead pitch of the second thread. Without being limited, it is believed that having the same lead pitch may reduce backdrive more efficiently than having different lead pitches.

Manual Brake Release

In some embodiments, the self-centering ball screw assembly includes a manual brake release. The manual brake release is configured to release a brake of the self-centering ball screw assembly such that a vertical position of the manipulatable arm can be adjusted manually.

In some embodiments, the counter-weighted Z drive would be combined with a standard electromechanical brake, such that the manipulatable arm 28 is held in place when system power is off. The release button can be located in a position convenient to the user. The release button can for example be designed as a trigger, combined with a pull handle that the user can push or pull (while holding the release button down) in order to change the vertical location of the robot arm 28.

Linear Encoder and Calibration Features

Position feedback can be accomplished using a linear encoder, for example, a Renishaw RESOLUTE linear encoder, with a precision bar-code scale mounted to one side of the ballscrew profile rail assembly, and the read head mounted to the top carriage. Redundant feedback may be implemented in a similar fashion, with an incremental linear encoder mounted to the opposite side of the profile rail assembly.

The self-centering ball screw assembly 200 can include a linear encoder (not shown) configured to provide linear position feedback. The linear encoder can be a sensor, transducer or readhead paired with a scale that encodes position. The sensor reads the scale in order to convert the encoded position into an analog or digital signal, which can then be decoded into position by a digital readout (DRO) or motion controller. The encoder can be either incremental or absolute. Motion can be determined by change in position of the assembly over time. The linear encoder can be optical, magnetic, inductive, capacitive or eddy current. An optical image sensor without a scale can be used based on an image correlation method. For example, the sensor can capture subsequent pictures from the surface being measured and compare the images for displacement.

The carriage(s) 220, 230 can include a calibration feature configured to measure and/or correct a position or alignment of the carriage. Measurements can be imported into a suitable type of software to plot the points or to calculate deviation from the correct position. A target reflects the laser beam back in the same direction it came from, for example, back to the laser tracker. One type of target in common use is a spherically mounted retroreflector (SMR), which resembles a ball bearing with mirrored surfaces cut into it. In some embodiments, the carriage includes SMR divots for a laser tracker.

Though not discussed in detail herein, it is contemplated that the Theta 1 drive motor can be mounted below the ball screw assembly 200 to reduce weight in the robot arm 28.

Digitizer

When combined with the direct-drive arm design (described in more detail below) this Z axis design allows use of the robot arm as its own digitizer probe. This will increase implant placement accuracy by eliminating the need to calculate and rely upon a coordinate transformation, for example, between the Microscribe and the robot arm, and will improve system usability by removing the Microscribe from the front of the robot.

Manipulatable Arm

Returning to FIGS. 4A and 4B, in a preferred embodiment, the manipulatable arm includes two or more segments. A first segment has a first end and a second end opposite the first end of the first segment and a first spindle rotatably coupling the first end of the first segment to a base segment. A second segment has a first end and a second end opposite the first end of the second segment and a second spindle rotatably coupling the first end of the second segment to the second end of the first segment. In some embodiments, the manipulatable arm includes a third segment having a first end and a third spindle rotatably coupling the first end of the third segment to the second end of the second segment. The manipulatable arm includes a plurality of drive assemblies including a first drive assembly positioned in the base segment to drive the first spindle, a second drive assembly positioned in the first segment to drive the second spindle and a third drive assembly positioned in the second segment to drive the third spindle. Each drive assembly encloses an end of a spindle and includes a rotor assembly having permanent magnets mounted on a respective spindle to be driven, and a stator assembly having a coil bracket surrounding the rotor assembly and enclosing one end of the respective spindle.

In a preferred embodiment, the first, second and third spindles have axes of rotation that are substantially parallel. As shown in FIG. 4B, the manipulatable arm includes rotary joints {theta1, theta2, roll} or {shoulder, elbow, wrist}, which operate in the horizontal (XY) plane. The drive assemblies (actuators or motors) of the segments drive each of the rotary joints. It will be appreciated from the disclosure herein that the horizontal motion is controlled by separate actuators than the vertical motion of the arm, and pitch motion of the wrist described above.

Each rotary axis can be a drive assembly. For example, each rotary axis has a single spindle (or motor shaft—for example 50 mm OD), which is directly coupled to a rotor, absolute ring encoder, and incremental (redundant) disk encoder.

In a preferred embodiment, the drive assemblies are direct drive assemblies. In some embodiments, the drive assemblies are frameless motors (also known as "kit" motors). Thus, at each of the rotary joints of the manipulatable arm, the motor and the joint form a single assembly, with no external drivetrain components needed. Each motor shaft has two widely separated angular contact bearings, capable of handling combined radial and thrust loads. Bearing preload can be set using a wave spring installed in the motor at the time of assembly. In some embodiments, these are the only bearings at each joint, so bearing performance may be easily modeled in advance.

Components can be axially located on motor shafts using snap rings and torque can be transferred from rotor to shaft using a coil spring pin. Other components can be radially and rotationally located using precision alignment pins (round and/or diamond profile).

The advantages of a frameless motor based, direct-drive design include for example, high stiffness, zero backlash, low parts count, high control authority, and extremely low backdriving torque. These advantages may enable further system-level design improvements including reduction of size and weight, improved manufacturability, decreased cost, improved motion control accuracy, and direct use of the robot arm in place of the Microscribe digitizer.

In some embodiments, the motor shafts (or spindles) are hollow. The hollow motor shaft can also be used as a cable passage. For example, in some embodiments, each spindle includes a hollow center that is configured for containing electrical or service lines.

The segments of the manipulatable arm can be arranged in any suitable configuration. For example, the first, second and third segments can be linked to one another in an ascending step configuration.

As shown in FIGS. 4A and 4B, the effector 32 can be mounted to the third segment.

Figure 8A:
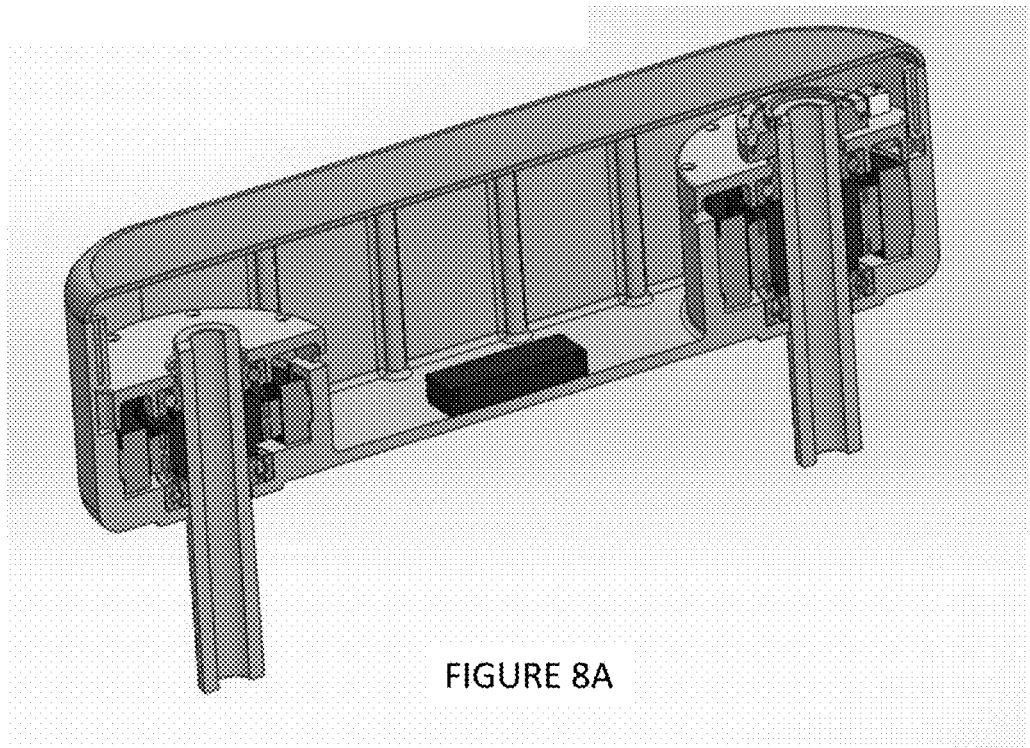
FIGS. 8A-8C illustrate a segment of a manipulatable arm of the robotic system.
Figure 8B:
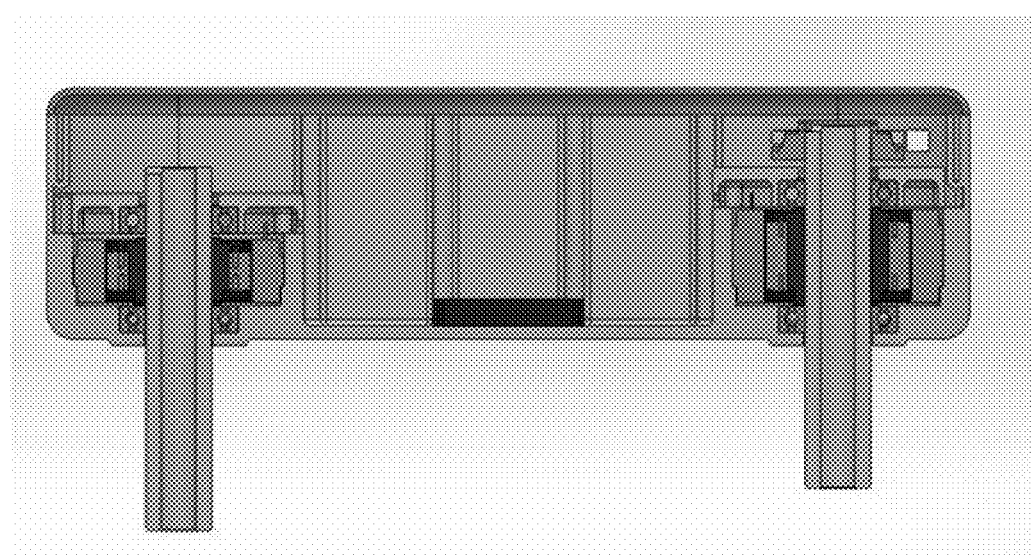
Figure 8C:
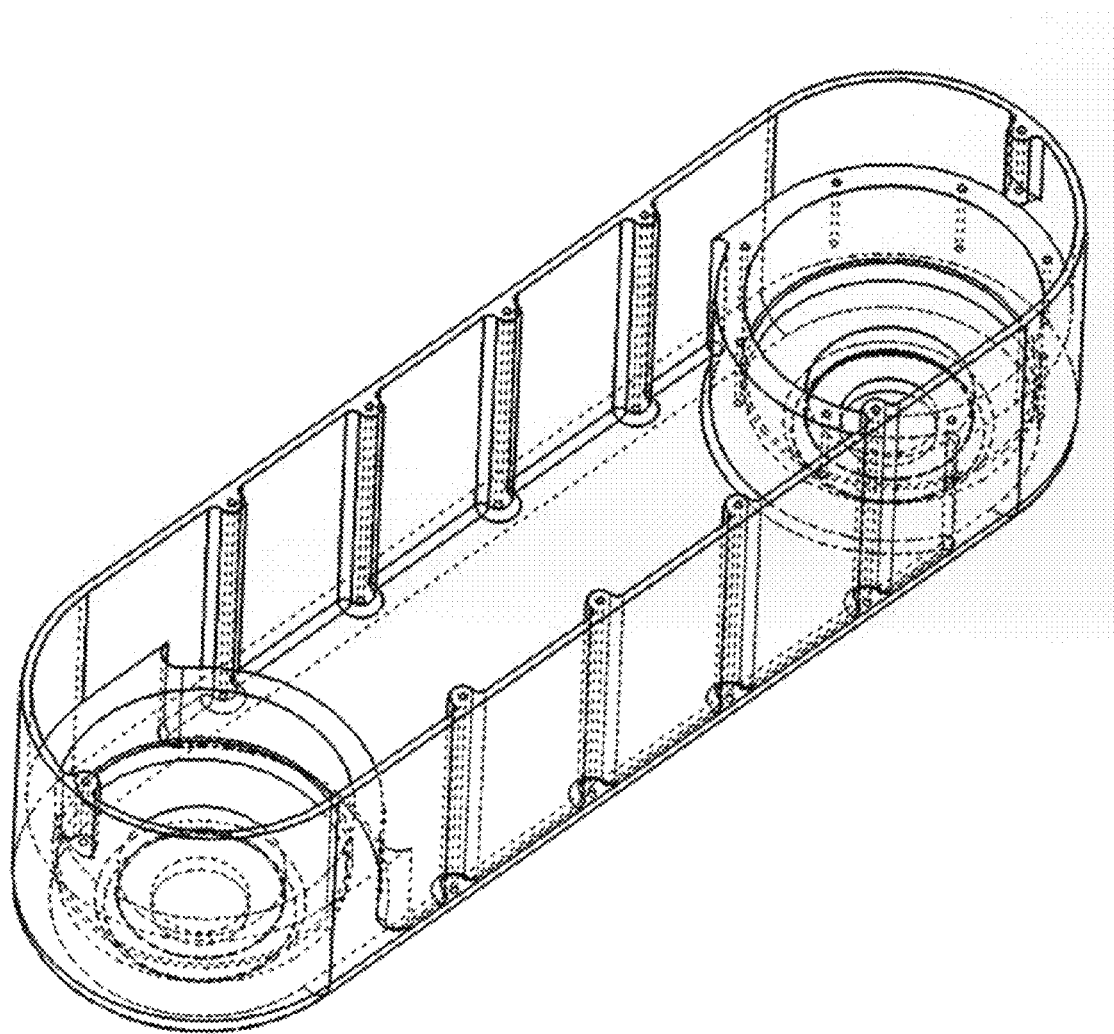

As shown in FIGS. 8A-8C, in a preferred embodiment, each of the segments (first segment, the second segment, and the third segment) is a single machined part configured to house or frame each of the drive assemblies (first direct drive assembly, the second direct drive assembly, and the third direct drive assembly).

For example, each segment can be machined to include mounting bores for the stator(s) of the frameless motor(s) installed in the segment. Stators can be permanently mounted by thermal shrink fit. Precise placement and alignment of stators, bottom bearings, and alignment pins can be ensured by creating all of the mounting features in a single CNC milling operation. In some embodiments, each segment is machined from any suitable material, such as aluminum.

Encoders

In some embodiments, the drive assemblies include one or more positional measurement apparatus. For example, in some embodiments, each direct drive assembly includes a positional measurement apparatus that is operative to ascertain an angular disposition of one segment relative to an adjoining segment.

The positional measurement apparatus can be selected from any suitable encoder. For example, the positional measurement apparatus can be a rotary optical encoder or a magnetic encoder, or the like.

For example, each rotary axis can include a high resolution (22 bit) RESOLUTE ring encoder which allows position repeatability. The positional repeatability can be as low as 10 um at the robot end effector.

In some embodiments, motion controllers are integrated into the segments of the manipulatable arm, with short cable runs to stators and encoders, for high noise immunity and reduced harness size (for routing back to the robot base).

In some embodiments, the manipulatable arm includes dedicated features for calibration and shipping. For example, the calibration features can include one or more mounting holes for magnetic SMR (spherically mounted retroreflector) nests on each segment of the arm. When SMR targets are installed, a precision laser tracker may be used to measure the D-H parameters of the arm.

The arm can include dedicated features for shipping (fast pins/clips) and calibration (SMR divots for laser tracker). In some embodiments, holes are machined into the arm for ball-detent fast-pins that can lock the segments of the arm in place when folded, this can help reduce the backdrive of the arm.

In some embodiments, the system includes a system controller as described in commonly owned U.S. Pat. No. 5,806,518. The system controller positions the effector by moving the manipulatable arm.

In some embodiments, the end effector 32 is a rotary cutter, such as a disk cutter or a ball cutter as described in commonly owned U.S. Pat. No. 5,776,136.

In some embodiments, the system includes a six degree of freedom position sensor as described in commonly owned U.S. Pat. No. 6,332,567.

In some embodiments, the system includes a bone fixator as described in commonly owned U.S. Pat. No. 5,806,518.

In some embodiments, the system includes a bone digitizer arm as described in commonly owned U.S. Pat. Nos. 6,332,567 and 6,033,415.

In some embodiments, the system includes a plurality of position sensors for generating a digitized bone data set as described in commonly owned U.S. Pat. No. 6,033,415.

In some embodiments, the system includes a non-contact digitizing apparatus to generate a digitized bone data set as described in commonly owned U.S. Pat. No. 6,033,415.

In some embodiments, the system includes an angle indicator attached to the arm as described in commonly owned US Patent Publication No. 2011/0152871.

In some embodiments, the system includes an impactor physically connected to an angle indicator with at least one flexible guide as described in commonly owned US Patent Publication No. 2011/0152871.

Additional Features

The design approach described herein may also make the surgical robotic system suitable for operation in clean rooms or other sensitive environment, as cables are routed internally through hollow shafts and the harness footprint is kept to a minimum due to the distributed motion controller placement.

In some embodiments, it may be possible to design the robot wrist to include a hollow bore (e.g., roughly 10 mm) which could be used to pass irrigation fluid or pneumatic power.

It may be possible to use slip ring contacts for continuous rotation at the robot elbow and wrist, eliminating significant kinematics singularities.

Although discussed with respect to a surgical robotic system, a robot system as disclosed could be used for a variety of other computer-controlled precision tasks, including laser cutting, plasma cutting, additive fabrication (3D printing, laser sintering), plotting/drawing, routing or milling with other rotary tools, pick-and-place for printed circuit assembly, part sorting or packaging, biomedical sample handling, automated laboratory experiments (precision dispensing of reagents), part assembly, welding, painting, polishing, etc.

The ability of the arm to be easily backdriven could be applied to other fields (such as assembly line work) by allowing the arm to be easily guided by hand in a "teach" mode, whereby the robot may "learn" to perform repetitive tasks. The presence of medical-grade safety features such as redundant encoders might make the arm safe enough for hand guiding even in heavy industry applications.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A surgical robotic system comprising:
   a manipulatable arm that carries a movable effector;
   a counterbalanced Z-axis drive, wherein the counterbalanced Z-axis drive includes a self-centering ball screw assembly having a first carriage configured to carry the manipulatable arm and a second carriage configured to carry a counter weight and wherein the counterbalanced Z-axis drive controls at least one of the manipulatable arm or the movable effector.

2. The system of 1, wherein the self-centering ball screw assembly includes a shaft haying a first portion with a first thread and a second portion with a second thread in a direction opposite the first thread, wherein the first carriage engages the first portion of the shaft and the second carriage engages the second portion of the shaft.

3. The system of claim 2, wherein a lead pitch of the first thread is larger than a lead pitch of the second thread.

4. The system of claim 1, wherein the first carriage of the self-centering ball screw assembly includes a linear direct drive actuator.

5. The system of claim 1, wherein the Z-axis drive controls the manipulatable arm and the movable effector.

6. The system of claim 1, further comprising a linear encoder configured to provide linear position feedback.

7. The system of claim 1, wherein the counter weight is configured to substantially support a load associated with the manipulatable arm when the driving portion is engaged or disengaged.

8. The system of claim 1, further comprising a manual brake release configured to release a brake of the self-centering ball screw assembly such that a vertical position of the manipulatable arm can be adjusted manually.

9. The system of claim 1, further comprising a system controller, wherein the controller positions the effector by moving the manipulatable arm further comprising a rotary cutter, such as a disk cutter or a ball cutter.

10. The system of claim 1, further comprising a six degree of freedom position sensor.

11. An improved robotic system of the type having a manipulatable arm which carries an effector and a programmable controller which positions the effector within a robotic coordinate system, wherein the improvement comprises:
a counterbalanced Z-axis drive omprising a self-centering ball screw assembly having first carriage configured to carry the manipulatable arm and a second carriage configured to carry a counter weight.

12. A surgical robotic system comprising:
a manipulatable arm that carries a movable effector;
a counterbalanced Z-axis drive, wherein the counterbalanced Z-axis drive includes a self-centering bail screw assembly and wherein the counterbalanced Z-axis drive controls at least one of the manipulatable arm or the movable effector, wherein the manipulatable arm comprises:
a first segment having a first end and a second end opposite the first end of the first segment;
a first spindle rotatably coupling the first end of the first segment to a base segment;
a second segment having a first end and a second end opposite the first end of the second segment;
a second spindle rotatably coupling the first end of the second segment to the second end of the first segment;
a third segment having a first end; a third spindle rotatably coupling the first end of the third segment to the second end of the second segment; and
a plurality of direct drive assemblies including:
a first direct drive assembly positioned in the base segment to drive the first spindle,
a second direct drive assembly positioned in the first segment to drive the second spindle, and
a third direct drive assembly positioned in the second segment to drive the third spindle, each direct drive assembly encloses an end of a spindle and comprises a rotor assembly having permanent magnets mounted on a respective spindle to be driven, and a stator assembly having a coil bracket surrounding the rotor assembly and enclosing one end of the respective spindle.

13. The system of claim 12, wherein each of the first segment, the second segment, and the third segment is a single machined part configured to house/frame each of the first direct drive assembly, the second direct drive assembly, and the third direct drive assembly.

14. The system of claim 12, wherein each direct drive assembly of the manipulatable arm further includes a positional measurement apparatus that is operative to ascertain an angular disposition of one segment relative to an adjoining segment.

15. The system of claim 14, wherein the positional measurement apparatus comprises a rotary optical encoder or a magnetic encoder.

16. The system of claim 12, wherein the first, second and third spindles have axes of rotation that are substantially parallel.

17. The system of claim 12, wherein the third segment is mounted with the effector.

18. The system of claim 12, wherein the first, second and third segments are linked to one another in an ascending step configuration.

19. The system of claim 12, wherein each spindle includes a hollow center that is configured for containing electrical or service lines.

* * * * *